United States Patent [19]

Sibbald et al.

[11] Patent Number: 5,412,463
[45] Date of Patent: May 2, 1995

[54] FINGER GUIDE WITH ORTHOGONAL GUIDE SURFACES

[75] Inventors: Alastair Sibbald, Maidenhead; Michael Jackson; Elaine Jackson, both of Hayes; Terence Dean, Ruislip, all of Great Britain

[73] Assignee: Central Research Laboratories Limited, Middlesex, England

[21] Appl. No.: 72,383

[22] Filed: Jun. 7, 1993

[30] Foreign Application Priority Data

Jun. 6, 1992 [GB] United Kingdom ............... 9212066

[51] Int. Cl.⁶ .................. G06K 9/20; G06K 9/74
[52] U.S. Cl. ............................ 356/71; 382/126
[58] Field of Search ............ 356/71; 382/2, 4, 5

[56] References Cited

U.S. PATENT DOCUMENTS

| | | | |
|---|---|---|---|
| 4,053,228 | 10/1977 | Schiller | 356/71 |
| 4,905,293 | 2/1990 | Asai et al. | 356/71 |
| 4,946,276 | 8/1990 | Chilcott | 356/71 |
| 5,187,748 | 2/1993 | Lee | 382/4 |

FOREIGN PATENT DOCUMENTS

| | | | |
|---|---|---|---|
| 61-175866 | 8/1986 | Japan | 382/4 |
| 2-307175 | 12/1990 | Japan | 382/4 |
| 3-36680 | 2/1991 | Japan | 382/4 |
| 3-92983 | 4/1991 | Japan | 382/4 |
| 3-154182 | 7/1991 | Japan | 382/4 |
| 3-156691 | 7/1991 | Japan | 382/4 |
| 3-226888 | 10/1991 | Japan | 382/4 |

*Primary Examiner*—Rolf Hille
*Assistant Examiner*—Minhloan Tran
*Attorney, Agent, or Firm*—Keck, Mahin & Cate

[57] ABSTRACT

A finger guide (2) comprises first and second orthogonally-oriented portions (4,12) each comprising a pair of opposed converging surfaces (6,8;14,16) into which the end and the shank, respectively, of a finger for examination fit. Because of the relative orientation of the surfaces, movement of the finger relative to an examination surface (22) is reproducibly constrained.

5 Claims, 2 Drawing Sheets

FINGER GUIDE WITH ORTHOGONAL GUIDE SURFACES

I. BACKGROUND OF THE INVENTION

A. Field of the Invention

The present invention relates to a finger guide and has particular, although not exclusive, relevance to the employ of such guides in fingerprint recognition systems, access control systems and the like.

B. Description of the Related Art

The need to accurately position a finger in order to examine its fingerprint is well known. The reason for this is that in, say, an access control environment, where the fingerprint under examination will be compared with a library of known fingerprints, unless the fingerprint is accurately aligned with the apparatus providing the examination in strict accordance with the same alignment as used for supplying the initial fingerprint in the library, then a match may not be recognised by the access controller even though the same fingerprint is actually present.

Solutions to this problem do exist, such as described in U.S. Pat. No. 4,053,228.

In this document a "fingerpress" is described. This fingerpress comes about when a finger whose print is to be imaged is pressed against the rear surface of a transparent glass plate and held in a predetermined position thereon. Problems exist with such an arrangement, however. Because the fingerprint is essentially a rectangular cavity providing little or no support to the finger, the onus of accurately positioning the finger against the plate lies firmly with the person whose fingerprint is to be obtained.

A finger guide which allows for automatic accurate and reproducible alignment of a given finger without the need to rely upon the manual dexterity of the person whose fingerprint is to be examined is an attractive proposition. Indeed, this is an object of the present invention.

II. SUMMARY OF THE INVENTION

Hence, according to the present invention, there is provided a finger guide for reproducibly guiding a given finger to the same position relative to a substantially flat fingerprint examination surface, the guide comprising a first guide portion having a stop for the end of the finger and a first pair of opposed guide surfaces for receiving the end of the finger and guiding it towards the stop to a position at which it bears against the stop and both guide surfaces and the pad bears on the examination surface, and a second guide portion for simultaneously receiving a part of the finger remote from the finger end to orient the finger in a given direction relative to the stop, which second guide portion has a second pair of opposed guide surfaces which are substantially planar, and which converge towards the plane of the examination surface, for guiding the remote part of the finger towards the plane to a position at which it bears against both surfaces, the stop extending in a direction perpendicular to the plane insufficiently far to obstruct the nail of the finger.

Hence, the present invention provides a finger guide wherein the end of the finger may be guided to a central location and the shank of the finger may be held along a central axis. This combination of features provides that any given finger will automatically assume substantially the same position any time it is presented to the finger guide.

Preferably the first and second pairs of surfaces are planar surfaces. This provides for only a minimal area of contact between the finger and any one surface, thereby providing a low-friction contact to aid ease of movement when presenting the finger to the finger guide and removing the finger therefrom. Alternatively, the first portion may comprise a resilient member having a substantially 'U' shape. Additionally, the first and second portions may be oriented such that the first pair of surfaces converge in a direction orthogonal to the direction of convergence of the second pair of surfaces. This allows for an efficient constraining of the finger as compared with hitherto known prior art.

III. BRIEF DESCRIPTION OF THE DRAWINGS

The invention will now be described by way of example only and with reference to the following two illustrative embodiments as detailed in the following drawings of which:

IV. DESCRIPTION OF THE PREFERRED EMBODIMENTS

Figure 1:
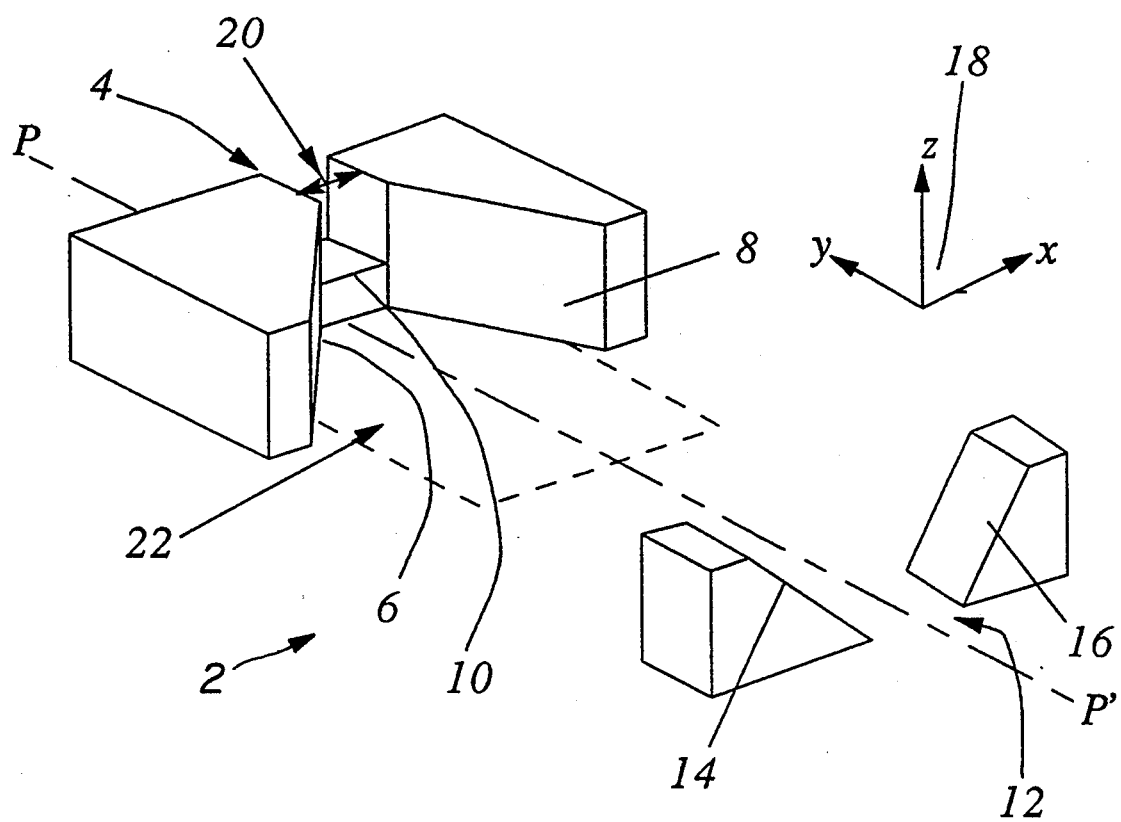
FIG. 1 shows a perspective view of a first embodiment of a finger guide in accordance with the present invention.

Referring firstly to FIG. 1 it will be seen that a finger guide in accordance with the present invention comprises a first portion 4 having a pair opposed of guide surfaces 6,8 which converge towards and end stop 10, and a second portion 12 comprising a pair of opposed guide surfaces 14,16. Both portions 4,12 are mounted so as to lie on a plane (the x-y plane as shown by the co-ordinate axes 18) in which an examination surface 22 also lies. The surfaces 14,16 of the second portion 12 converge towards the x-y plane. The end stop 10 extends in the z direction, perpendicular to the x-y plane, insufficiently far to obstruct the nail of a finger, terminating in a cavity 20 between the first surfaces 6,8. This is necessary because the guide 2 must be able to accommodate a broad range of finger sizes and shapes.

A finger (not shown) whose fingerprint is to be examined is presented to the guide 2 such that the end of the finger is urged into engagement with the first portion 4. The tip of the finger abuts the end stop 10 whilst only a small area of contact exists between each side of the finger and a respective surface 6,8. In this manner, the fingerprint to be examined will lie on the examination surface 22. Next a part of the shank of the finger which is remote from the finger end is urged into the second portion 12, in between the second guide surfaces 14,16. Once again, only a small area of contact exists between each side of the shank and a respective surface 14,16.

The advantage of retaining a finger within the guide will be explained below.

It can be seen from FIG. 1 that the first and second pairs of surfaces (6,8;14,16) are oriented orthogonally with respect to one another. Furthermore, they are symmetrical about axis P-P$^1$. It is in the direction of this axis P-P$^1$ that the finger when presented to the guide, is to lie. It can also be seen that the first surfaces 6 and 8 are arranged to substantially face the direction from which the finger will be moved into the guide, i.e. along P-P$^1$. Hence, when presented to the first portion 4, the end of the finger is tangentially forced into a central position with respect to the axis P-P$^1$ by the "funnelling" action of surfaces 6,8. In the example detailed in FIG. 1, the surfaces 6,8 are inclined to each other at an angle of 70°. In such circumstances where the end of the finger has a protruding fingernail, then this is accommodated within the cavity 20.

Because the surfaces 14, 16 of second portion 4 are symmetrical about axis P-P$^1$, when the finger shank is pressed therebetween, the shank is aligned along this axis. Once again, the angle between the second surfaces 14,16 is, in this example, chosen to be 70°.

In FIG. 1, the surfaces of both portions 4,12 have been shown as flat, planar members. This is chosen so as to provide a minimal area of contact between the finger and each respective surface 6,8,14,16, so that movement of the finger when being presented to and removed from the guide is an uninhibited as possible. However, when the finger is in place, it will be realised that movement in directions parallel to the x-y plane is constrained and hence the finger is held in position.

It will also be apparent that by suitable design of the portions 4, 12, any size or shape of a normal adult finger may be accommodated. Furthermore any given finger, when presented to the guide, will assume substantially the same position relative to both wedges, whenever it is presented. This principle is illustrated with reference to FIGS. 2(a) and 2(b) where it can be seen that a wide finger 24 will always be held within the first portion 4 near the point of maximum separation of the first surfaces 6,8 whereas a narrow finger 26 will always be held within the portion 4 near the point of minimum separation of the surfaces 6,8.

Figure 2:
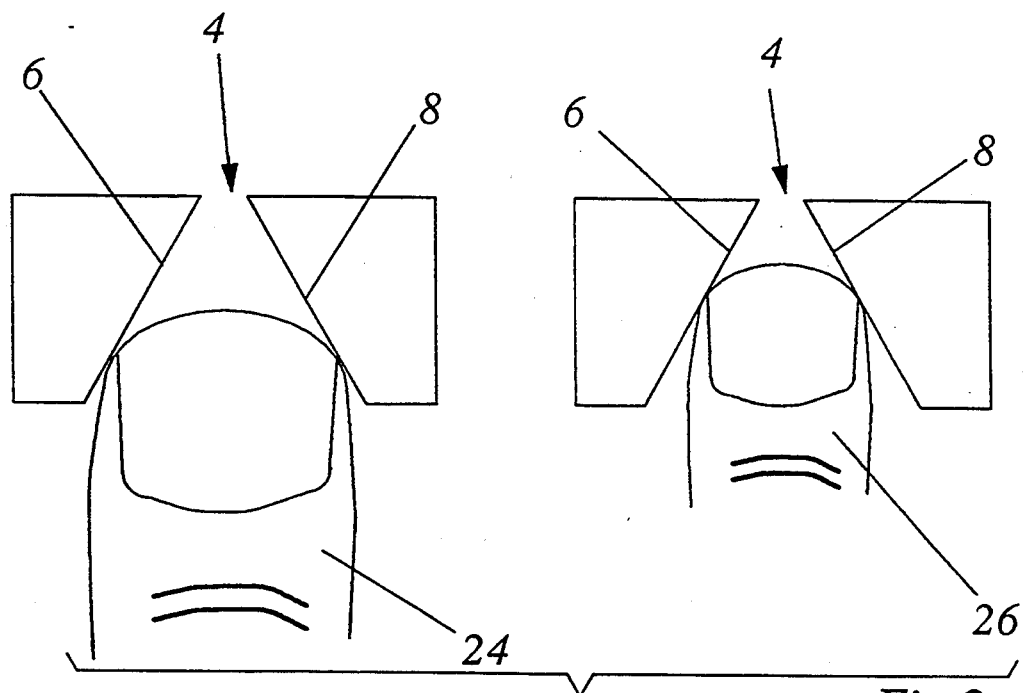
FIG. 2 shows a wide and a narrow finger being accommodated within a guide in accordance with the present invention.

The principle of employing converging planar guide surfaces as illustrated in FIGS. 1 and 2 also permits the pad of the finger whose fingerprint is to be examined to expand laterally on the examination area 22 as there are only two small areas at which the sides of the finger actually engage with each of surfaces 6,8 as detailed herebefore.

Figure 3:
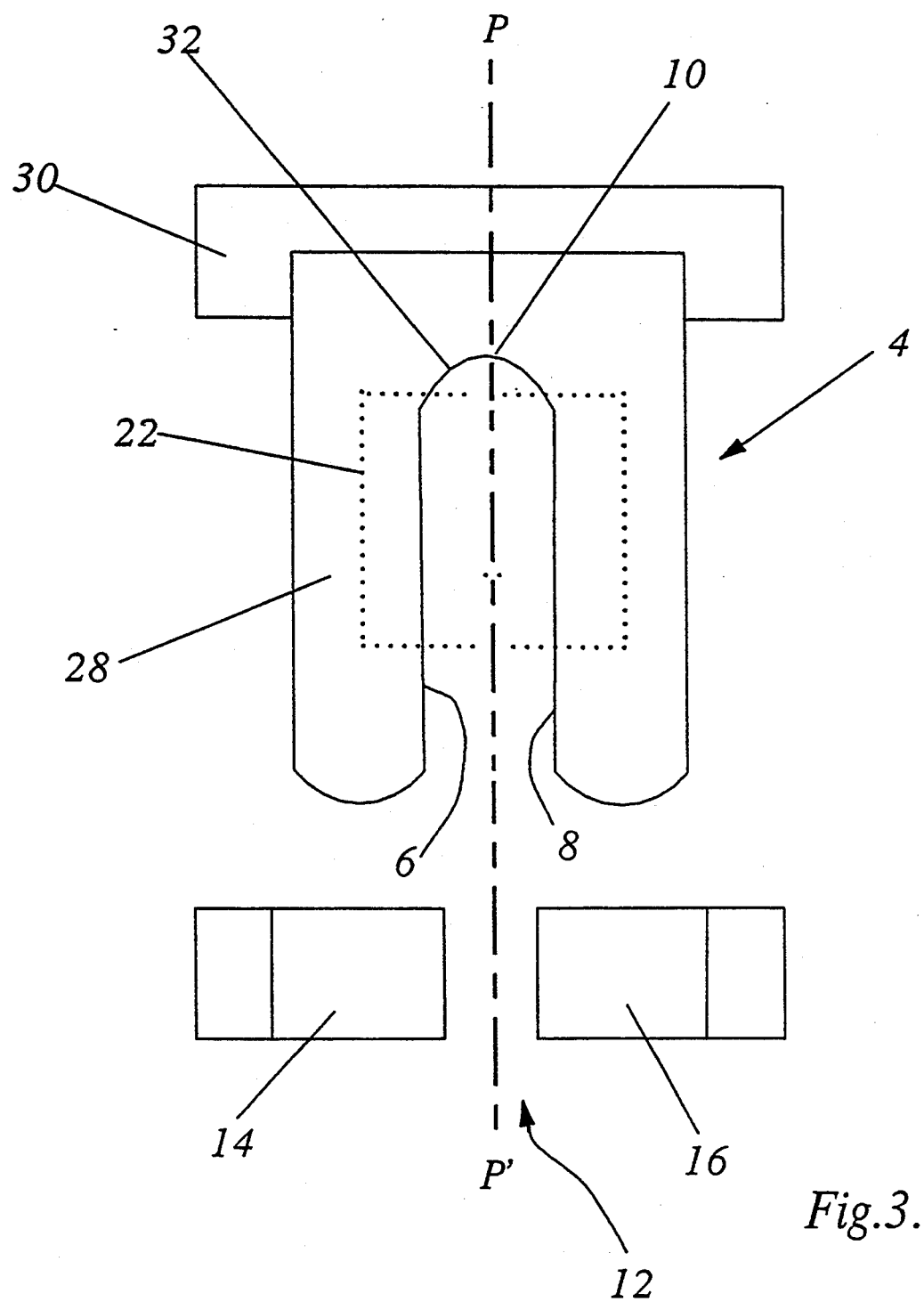
FIG. 3 shows a schematic representation of a second embodiment of a finger guide in accordance with the present invention.

Referring now to FIG. 3, an alternative embodiment to that of FIG. 1 is illustrated, wherein similar components are referenced with like reference numerals.

It will be seen that the first portion comprises a resilient member 28, for example of a foam material in the form of a "U" shape, which resilient member 28 is coupled to, and supported along the base of the "U" by, supporting means such as support bar 30.

Opposed guide surfaces 6,8 of the resilient member 28 are formed by the inner surfaces of the arms of the "U" shape. The arms are parallel and free to deform outwardly at their extremities, and converge towards the end stop 10 in an arc 32. Thus, by analogy with the above description relating to FIG. 1, a finger inserted into the resilient member 28 along the axis P-P$^1$ will be centralised along the axis P-P$^1$ by the surfaces 6,8. The resilient member 28 may deform sufficiently to conform to the contours of the finger thereby to form a snug fit around the finger and constrain the finger therewithin.

Whilst it will be appreciated that the area of contact between each side of the finger and each surface 6,8, is greater than that of the previous embodiment, the effect achieved by employing a resilient member 28 is functionally equivalent to that achieved by the first guide portion 4 of FIG. 1. The pad of the finger may expand laterally on the examination area 22 due to the resiliance of the foam member 28.

Moreover, any given finger presented to guide by way of the resilient member 28 will assume substantially the same position whenever this given finger is presented. It has been found that the dimensions of normal adult fingers, with which a guide in accordance with the present invention must co-operate, may vary from an end width of between about 10 mm to 20 mm and a shank width of between around 15 mm to 40 mm.

It will thus be understood that a finger guide in accordance with the present invention as compared with hitherto known finger guides provides a more reproducible constraint with less opportunity for the finger to move out of position.

In any event, it will be understood that when first guide portion 4 of FIG. 1 or the resilient member 28 of FIG. 3 receives the end of a finger presented thereto, the finger contacts surfaces 6,8 before contacting the end stop 10.

Similarly, when the shank of the finger is received by the second portion 12, the shank will contact surfaces 14,16 before intersecting and/or contacting the x-y plane.

We claim:

1. A finger guide for reproducibly guiding a pad of a given finger to the same position relative to a substantially flat fingerprint examination surface, the guide comprising a first guide portion having an end stop for the end of the finger and a first pair of opposed guide surfaces for receiving the end of the finger and guiding it towards the end stop to a position at which it bears against the end stop and both guide surfaces and the pad bears on the examination surface, and a second guide portion for simultaneously receiving a part of the finger remote from the finger end to orient the finger in a given direction relative to the end stop, which second guide portion has a second pair of opposed guide surfaces which are substantially flat, and which converge towards the plane of the examination surface, for guiding the remote part of the finger towards the plane to a position at which it bears against both guide surfaces, the end stop extending in a direction perpendicular to the plane insufficiently far to obstruct the nail of the finger, the first and second pairs of guide surfaces are oriented substantially orthogonally with respect to each other.

2. A finger guide according to claim 1, wherein the first pair of guide surfaces are substantially flat.

3. A finger guide according to claim 1, wherein the first portion comprises a resilient member having a substantially "U" shape.

4. A finger guide according to claim 1, wherein the first portion is arranged such that any given finger received within the first portion contacts the first pair of guide surfaces before contacting the end stop.

5. A finger guide according to claim 1, wherein the second portion is arranged such that any given finger received within the second portion contacts the second pair of surfaces before intersecting the predetermined plane.

* * * * *